United States Patent [19]

Ciocca et al.

[11] Patent Number: 4,814,000
[45] Date of Patent: Mar. 21, 1989

[54] STABILIZED HERBICIDE COMPOSITION BASED ON META-BISCARBAMATES

[75] Inventors: Baldo Ciocca, Milan; Attilio Formigoni, Legnano; Gino Epis, Lodi, all of Italy

[73] Assignee: S.I.P.C.A.M. S.p.A - Societa Italiana Prodotti Chimici e per l'Agricoltura Milano, Milan, Italy

[21] Appl. No.: 902,131

[22] Filed: Sep. 2, 1986

Related U.S. Application Data

[63] Continuation-in-part of Ser. No. 750,254, Jul. 1, 1985, abandoned, which is a continuation-in-part of Ser. No. 521,836, Aug. 10, 1983, abandoned.

[30] Foreign Application Priority Data

Aug. 13, 1982 [IT] Italy ................. 22837 A/83
Jul. 13, 1983 [IT] Italy ................. 22041 A/83

[51] Int. Cl.$^4$ ............................. A01N 25/22
[52] U.S. Cl. ..................... 71/111; 71/DIG. 1
[58] Field of Search .................. 71/DIG. 1, 111

[56] References Cited

U.S. PATENT DOCUMENTS

| | | | |
|---|---|---|---|
| 3,404,975 | 10/1968 | Wilson et al. | 71/111 |
| 3,898,075 | 8/1975 | Freund et al. | 71/111 |
| 4,202,684 | 3/1980 | Arndt et al. | 71/111 |
| 4,252,557 | 2/1981 | Boroschewski et al. | 71/111 |
| 4,257,804 | 3/1981 | Arndt et al. | 71/111 |
| 4,313,847 | 2/1982 | Chasin et al. | 71/111 |
| 4,315,769 | 2/1982 | Boroschewski et al. | 71/111 |
| 4,441,915 | 4/1984 | Arndt et al. | 71/111 |
| 4,461,641 | 7/1984 | Abildt et al. | 71/DIG. 1 |

FOREIGN PATENT DOCUMENTS

| | | | |
|---|---|---|---|
| 57-58601 | 4/1982 | Japan | 71/111 |
| 1193998 | 6/1970 | United Kingdom | 71/111 |

OTHER PUBLICATIONS

Bachelot et al., "Aqueous Insecticide, etc.," (1981) CA 95:163933g (1981).

*Primary Examiner*—Catherine L. Mills
*Attorney, Agent, or Firm*—Stevens, Davis, Miller & Mosher

[57] ABSTRACT

A chemically stabilized herbicide composition containing the compound with the formula:

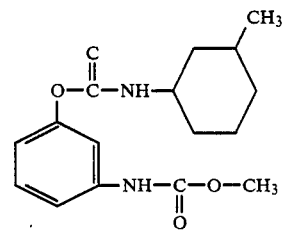

together with tristyryl-phenol-phosphates-polyethoxylated and/or polypropoxylated as well as with other possible coadjuvant and inert substances.

7 Claims, No Drawings

STABILIZED HERBICIDE COMPOSITION BASED ON META-BISCARBAMATES

This application is a continuation-in-part of application Ser. No. 750,254 filed July 1, 1985 which in turn is a continuation-in-part of application Ser. No. 521,836 filed Aug. 10, 1983, now abandoned.

BACKGROUND OF THE INVENTION

This invention relates to a chemically stabilised herbicide composition based on meta-biscarbamates.

It is known that herbicide composition containing a compound of formula:

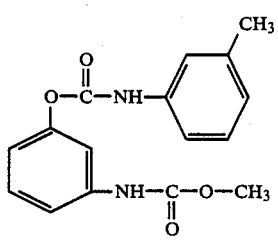
(A)

or 3-methoxycarbonyl-aminophenyl-N-(3-methylphenyl)carbamate possess excellent herbicide action on sugar beet and other crops, if formulated with suitable adjuvants and inerts.

However, it is also known that the aforesaid compounds possess limited chemical stability with time if prepared in common emulsifiable liquid herbicide compositions based on organic solvents, and which contain adjuvants having no stabilising effect.

U.S. Pat. No. 3,898,075 describe the possibility of stabilising the compound of formula (A) in emulsifiable liquid herbicide compositions based on organic solvents, by adding a chemical stabilising compound chosen from dicarboxylic aliphatic acids, hydrocarboxylic aliphatic acids, nitro-substituted monocarboxylic aromatic acids, dicarboxylic aromatic acids, sulphonated aliphatic acids, and sulphonated aromatic acids. In addition to claiming these stabilisers, the aforesaid U.S. Patent described the already known addition of common surfactants and inerts commonly used by the expert in this field for preparing emulsifiable liquid composition suitable for use as plant protection products.

Specifically, stated suitable inerts are solvents based on aromatic hydrocarbons, cyclohexanone, isophorone, methylhexahydronaphtalene, dibutylphthalate, tetrahydrophthalene, dimethylsulphoxide and dimethylformamide, and stated suitable surfactants not acting as chemical stabilizers are polyethoxylated amines, alcohols, acids and alkylphenols, and salts of alkylbenzene and naphthalenesulphonic acids.

SUMMARY OF THE INVENTION

With the present invention, it has been unexpectedly found that the compound of formula

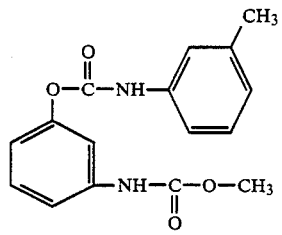
(A)

formulated as emulsifiable liquid, can be chemically stabilized with the addition to the formulation of tri-styryl-phenol-phosphates polyethoxylated and/or polypropoxylated, containing 6-25 moles of ethylene oxide and/or propylene oxide (in ratio of from 10:1 to 1:1 if both oxides are present).

Examples of the aforesaid stabilizers, which are usable in organic solvent-based emulsifiable liquid formulations are:

1. tristyril-phenol-phosphates-polyethoxylated with 17 moles of ethylene oxide (available commercially for example under the names SOPROPHOR 3D33 or SOPRAL 3D 33 or Messrs. SOPROSOIE CO. of Rochetaillee, France, or under the name SOITEM 8 FL of Messrs. SOITEM CO. Milan, Italy);

2. Tristyryl-phenol-phosphate-polyethoxylated with 6 moles of ethylene oxide (available commercially as SOITEM 3 FL of Messrs. SOITEM CO., Milan, Italy).

3. Tristyryl-phenol-phosphate-polypropoxylated with 25 moles of propylene oxide (available commercially as SOITEM 25 P of SOITEM CO. Milan, Italy).

4. A mixture of tristyril phenol phosphates polyethoxylated and polypropoxylated, with 20 moles of ethylene oxyde and 5 moles of propylene oxide (available commercially as SOITEM 8 EP of Messrs. SOITEM CO. Milan, Italy).

With respect to the previous known art, the interest of the present invention is even greater when considering that the tristyryl phenol phosphates polyethoxylated and/or polypropoxylated—cited hereabove—able to exhibit a chemical stabilising effect, also possess the property of acting as surfactants, ie as emulsifying agents, in herbicide formulations of emulsifiable liquids based on compound of formula (A), with obvious saving in adjuvants and greater composition economy.

The discovery was completely unattended because the surfactants used by the prior art for emulsifiable liquid compositions based on compound of formula (A), surfactants that can be eventually used also for increasing the biological activity of the compound of formula (A), are chemically different from those claimed in the present invention and—above all—do not show chemical stabilising activity on emulsifiable liquid compositions of compounds of formula (A) as demonstrated in the Table No. 1.

Additionally, it is known that some inorganic and/or organic acids are not active as stabilizers of emulsifiable liquid compositions of the compound of formula (A) and particularly the phosphoric acid, or acetic acid, do not act as stabilizers, as documented in Table No. 1.

Furthermore phenol derivatives as tristyryl-phenol are not active as stabilizers of compositions of formula (A), as reported also in Table No. 1. To the contrary the tri-styryl-phenol phosphates polyethoxylated and/or polypropylated of the invention are particularly active as stabilizers (see Table No. 1).

TABLE NO. 1

Stabilizing activity of some compounds on the emulsifiable liquid composition, having following ingredients:

(1) Active Substance: Compound of formula (A) of 97% purity 172 g
(2) Surfactants: as reported, in weight
(3) Stabilizers: as reported, in weight
(4) Solvent: Isophorone up to 1000 g

| Surfactants | Possible Stabilizers | T° | % Decomposition of Compound of formula (A) after 1 month | 3 months |
|---|---|---|---|---|
| 20% of a mixture of Polethoxylated alkylphenol, polyethoxylated fatty acid, and calcium dodecyl benzensulfonate | None | 20° C. | 3 | 10 |
| | | 54° C. | 30 | 60 |
| | +1% of phosphoric acid | 20° C. | 5 | 9 |
| | | 54° C. | 30 | 55 |
| | +1% of acetic acid | 20° C. | 6 | 12 |
| | | 54° C. | 33 | 65 |
| | +3,5% of tristyryl-phenol | 20° C. | 8 | 14 |
| | | 54° C. | 35 | 73 |
| 3.5% tristyrylphenolphosphate polyethoxylated with 17 moles of ethylene oxide (according to the invention) +1.5% calcium dodecylbenzene sulfonate | | 20° C. | <0.1 | <0.2 |
| | | 54° C. | <0.5 | <1 |
| 9.5% tristyrylphenolphosphate polyethoxylated with 20 moles of ethylene oxide and polypropoxylated with 5 moles of propylene oxide (according to the invention) | | 20° C. | <0.1 | <0.2 |
| | | 54° C. | <0.5 | <1 |
| 15% tristyrylphenolphosphate polypropoxylated with 25 moles of propylene oxide (according to the invention) | | 20° C. | <0.1 | <2 |
| | | 54° C. | <0.5 | <1 |

It is totally unattended that tri-styryl-phenol-phosphates polyethoxylated, show high stabilizing activity on the compound of formula (A), whereas both trystyrilphenol and phosphoric acid do not show any stabilizing effect.

Moreover, all the stabilisers according to the invention exhibit their activity in relatively small doses, for the most part economical. In this respect, said stabilisers can be added to the compound of formula (A) in a ratio that can be varied between 1:10 and 2.5:1, according to the type of formulation and the concentration of the compound of formula (A). In addition to the stabilisers, with possible surfactant effect according to the invention, other surfactants, suspending agents or emulsifying agents can be added to formulations of the compound of formula (A), as necessary for optimising the hydrophilic/lipophilic balance of the composition in accordance with the methods well known to the skilled man of the art (for example calcium alkylarylsulphonate, polyethoxylated fatty acids, polyethoxylated alkylarylphenols and others, as described in the publication McCutcheon's—Detergent & Emulsifiers—1982 Annual—International Edition, Glen Rock (N.J.) U.S.A.).

Other active pesticides or adjuvant substances can also be added to the formulations according to the invention, in particular other herbicides, such as chloridazon, metamitron, ethofumesate, lenacil, cycloate, diallate, triallate, butachlor, metolachlor, trimexachlor and others. For organic solvent-based liquid formulations which are emulsifiable in water, the following composition can be used by way of example:

10-25% (preferably 15-20%) of active substance of formula (A);

1-25% (preferably 2-10%) of stabiliser, which may also possess emulsifying action, possibly together with a further surfactant not possessing stabilising activity.

Remainder to 100% of solvents, together with other emulsifiers, if necessary. The solvents used can be isophorone, cyclohexanone, aromatic hydrocarbons, naphta solvent, dimethylsulphoxide, dimethylformamide, N-methylpyrrolidone and others.

The composition according to the invention is particularly suitable for use in the selective weed control of agricultural or horticultural crops (such as sugar beet, fodder beet, red beet, spinach, strawberries, etc.) mainly in treatment after weeds emergence, by spraying dilute aqueous emulsions or suspension containing from 0.23 to 1.5 Kg/Ha of active substance.

The following examples are useful for better illustrating the invention, but do not limit its possible applications.

EXAMPLE NO. 1

The following substance are fed into a vessel fitted with a liquid stirrer, and are kept constantly mixed:

| | Formula I | Formula II |
|---|---|---|
| Compound of formula (A) with 97% purity | 17.2 Kg. | 17.2 Kg. |
| SOITEM 8 FL (1) | 7.0 Kg. | 1.7 Kg. |
| Calcium dodecylbenzenesulphonate | 3.0 Kg. | 1.0 Kg. |
| Naphta solvent | 3.0 Kg. | 10.0 Kg. |
| Isophorone | 69.8 Kg. | 70.1 Kg. |
| TOTAL | 100.0 Kg. | 100.0 Kg. |

| | Formula III | Formula IV |
|---|---|---|
| Compound of formula (A) with 97% purity | 17.2 Kg. | 17.2 Kg. |
| SOPROPHOR 3D33 (2) | 3.5 Kg. | 20.0 Kg. |
| SOITEM 101 (1) | 0.5 Kg. | 1.0 Kg. |
| SOITEM 990 (1) | 2.0 Kg. | 3.0 Kg. |

-continued

|  | Formula III | Formula IV |
|---|---|---|
| Naphta solvent | 3.0 Kg. | — |
| Isophorone | 73.8 Kg. | 58.8 Kg. |
| TOTAL | 100.0 Kg. | 100.0 Kg. |

|  | Formula V | Formula VI |
|---|---|---|
| Compound of formula (A) with 97% purity | 11.8 | 25.5 |
| SOITEM 8 EP (1) | 17.7 | — |
| SOITEM 3 FL (1) | — | 7.5 |
| SOITEM 101 (1) | 0.5 | 2.0 |
| SOITEM 990 (1) | 3.5 | 3.0 |
| Naphta solvent | 3.0 | 3.0 |
| Isophorone | 63.5 | 59.0 |
| TOTAL | 100.0 | 100.0 |

Various stabilized emulsifiable liquid formulations are thereby obtained, to be used as herbicides.

(1) Messrs. SOITEM Milan (Italy)
(2) Messrs. SOPROSOIE Rochetaillee (France)

EXAMPLE NO. 2

The chemical stability of the active substance is observed at various temperature levels (20° C., and 54° C.) for various lengths of time (1 month and 3 months) for organic solvent-based emulsifiable liquid formulations, according to the invention, as indicated in Example No. 1, compared with an emulsifiable liquid formulation without stabilisers and having the following composition:

| Compound of formula (A) with 97% purity | 17.2 Kg. |
|---|---|
| SOITEM 101 (mixture of 80% octylphenol polyethoxylated with 20 moles E.O. with 20% calcium dodecylbenzenesulfonate)[1] | 1.0 Kg. |
| SOITEM 990 (mixture of 25% octylphenol polyethoxylated with 20 moles E.O. with 75% calcium dodecylbenzenesulfonate)[1] | 7.0 Kg. |
| Isophorone | 74.8 Kg. |
| TOTAL | 100.0 Kg. |

[1]Produced by SOITEM, Milan (Italy)

After the aging test of 3 months the formulation samples were used in a field with sugar beets of variety Monogem as post-emergence herbicides at the dosage of 2 and 6 l/ha, there being present a mixed population of weeds represented in almost equal proportion by *Chenopodium album, Stellaria media, Capsella bursa-pastoris, Solanum nigrum*, in a young stage of growth.

Three weeks after the herbicidal treatments the percent reduction of treated weeds was compared to the percent reduction of untreated weeds. No damage to sugar beets with both rates of herbicides was observed. Such results were also reported in the Table No. 1.

From the results shown in Table No. 1, it can be seen that the addition of the chemical stabilisers, according to the invention, prevents the decomposition of the active substance and loss of good herbicidal activity of the formulations, even if the emulsifiable liquid formulation is kept at elevated temperature for a long period.

TABLE NO. 1

Stability of the active substance of formula (A) (3-methoxycarbonyl-aminophenyl-N-(3-methylphenyl) carbamate) in emulsifiable liquid compositions, without and with chemical stabilisers according to the invention, after 1 month and 3 months of aging at 20° C. or 54° C. and their activity as post-emergence herbicides after 3 months of aging.

| COMPOSITIONS | T° | % Decomp. active substance after 1 month | % Decomp. active substance after 3 months | % Activity on weeds after 3 months at 6 l/ha | % Activity on weeds after 3 months at 2 l/ha | % Damages on Sugar beets |
|---|---|---|---|---|---|---|
| Composition with stabiliser | 20° C. | <0.1 | <0.2 | 100 | 90 | 0 |
| Formula I (Example No. 1) | 54° C. | <0.3 | <1 | 99 | 82 | 0 |
| Composition with stabiliser | 20° C. | <0.1 | <0.2 | 99 | 88 | 0 |
| Formula II (Example No. 1) | 54° C. | <0.5 | <1 | 97 | 80 | 0 |
| Composition with stabiliser | 20° C. | <0.1 | <0.2 | 99 | 89 | 0 |
| Formula III (Example No. 1) | 54° C. | <0.5 | <2 | 98 | 82 | 0 |
| Composition with stabiliser | 20° C. | <0.1 | <0.2 | 100 | 92 | 0 |
| Formula IV (Example No. 1) | 54° C. | <0.3 | <1 | 98 | 86 | 0 |
| Composition with stabiliser | 20° C. | <0.1 | <0.2 | 95 | 82 | 0 |
| Formula V (Example No. 1) | 54° C. | <0.3 | <1 | 92 | 78 | 0 |
| Composition with stabiliser | 20° C. | <0.1 | <0.2 | 100 | 96 | 0 |
| Formula VI (Example No. 1) | 54° C. | <0.5 | <2 | 100 | 95 | 0 |
| Composition without stabiliser | 20° C. | 3 | <10 | 60 | 20 | 0 |
| Formula of (Example No. 2) | 54° C. | 30 | <60 | 25 | 5 | 0 |

Formula I with stabiliser is a preferred composition.

The results are shows in Table No. 2, from which it can be seen that the addition of the stabilisers, according to the invention, prevents the decomposition of the active substance, even if the emulsifiable liquid formulation is kept at elevated temperature for a long period.

TABLE NO. 2

Stability of the active substance of formula (A) (3-methoxycarbonyl-aminophenyl-N—(3-methylphenyl) carbamate) in emulsifiable liquid compositions, with and without stabilisers according to the invention.

| COMPOSITIONS | T° | % Decomposition active substance after 1 month | % Decomposition active substance after 3 months |
|---|---|---|---|
| Composition with stabiliser | 20° C. | <0.1 | <0.2 |
| Formula I (Example No. 1) | 54° C. | <0.3 | <1 |
| Composition with stabiliser | 20° C. | <0.1 | <0.2 |
| Formula II (Example No. 1) | 54° C. | <0.5 | <1 |
| Composition with stabiliser | 20° C. | <0.1 | <0.2 |
| Formula III (Example No. 1) | 54° C. | <0.5 | <2 |
| Composition with stabiliser | 20° C. | <0.1 | <0.2 |
| Formula IV (Example No. 1) | 54° C. | <0.3 | <1 |
| Composition with stabiliser | 20° C. | <0.1 | <0.2 |
| Formula V (Example No. 1) | 54° C. | <0.3 | <1 |
| Composition with stabiliser | 20° C. | <0.1 | <0.2 |
| Formula VI (Example No. 1) | 54° C. | <0.5 | <2 |
| Composition without stabiliser | 20° C. | 3 | <10 |
| Formula of (Example No. 2) | 54° C. | 30 | <60 |

We claim:

1. An herbicide composition with chemical stability of the active ingredient formulated as an organic solvent-base emulsifiable liquid comprising an effective amount of the compound of formula:

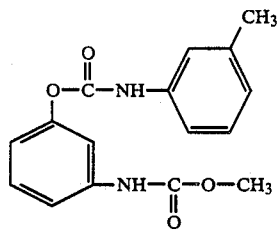

together with a chemical stabilizer selected from the group consisting of tristyryl-phenol-phosphate polyethoxylated, tristyryl-phenol-phosphate polypropoxylated and mixtures thereof along with other coadjuvants and inerts.

2. The composition as claimed in claim 1, wherein the tristyryl-phenol-phosphate polyethoxylated is formed from 6–25 moles of ethylene oxide.

3. The composition as claimed in claim 1, wherein the tristyryl-phenol-phosphate polypropoxylated is formed from 6–25 moles of propylene oxide.

4. The composition as claimed in claim 1 wherein the tristyryl-phenol-phosphate polyethoxylated and polypropoxylated have a ratio of 10:1 to 1:1 between ethylene oxide and propylene oxide.

5. The composition as claimed in claim 1 wherein the compound of formula A is contained in the quantity of 10 to 25 percent.

6. The composition as claimed in claim 1 wherein the ratio in weight between the stabilizer and the compound of formula A is comprised between 1:10 and 1.5:1.

7. Process for weed control comprising applying the composition of claim 1 at the rate from 0.23 to 1.5 kg per hectare to the weeds.